(12) United States Patent
Bloom

(10) Patent No.: US 8,901,073 B2
(45) Date of Patent: Dec. 2, 2014

(54) COMPOUNDS AND THEIR EFFECTS ON FEEDING BEHAVIOUR

(75) Inventor: Stephen Robert Bloom, London (GB)

(73) Assignee: Imperial Innovations Limited, London (GB)

( * ) Notice: Subject to any disclaimer, the term of this patent is extended or adjusted under 35 U.S.C. 154(b) by 0 days.

(21) Appl. No.: 13/982,125

(22) PCT Filed: Jan. 27, 2012

(86) PCT No.: PCT/GB2012/000086
§ 371 (c)(1),
(2), (4) Date: Jul. 26, 2013

(87) PCT Pub. No.: WO2012/101413
PCT Pub. Date: Aug. 2, 2012

(65) Prior Publication Data
US 2013/0303443 A1    Nov. 14, 2013

(30) Foreign Application Priority Data
Jan. 27, 2011 (GB) .................................. 1101459.4

(51) Int. Cl.
A61K 45/06 (2006.01)
C07K 14/575 (2006.01)
A61K 38/22 (2006.01)

(52) U.S. Cl.
CPC ............... C07K 14/575 (2013.01); A61K 38/22 (2013.01); A61K 45/06 (2013.01)
USPC .......................................... 514/5.2; 530/324

(58) Field of Classification Search
CPC .......... A61K 38/00; A61K 45/00; C07K 14/00
See application file for complete search history.

(56) References Cited

U.S. PATENT DOCUMENTS

| | | | |
|---|---|---|---|
| 4,179,337 | A | 12/1979 | Davis et al. |
| 5,936,092 | A | 8/1999 | Shen et al. |
| 6,093,692 | A | 7/2000 | Shen et al. |
| 6,225,445 | B1 | 5/2001 | Shen et al. |
| 6,355,478 | B1 | 3/2002 | Baez et al. |
| 6,410,707 | B2 | 6/2002 | Wagner et al. |
| 6,420,352 | B1 | 7/2002 | Knowles |
| 7,459,432 | B2 | 12/2008 | Cowley et al. |
| 7,666,835 | B2 | 2/2010 | Bloom et al. |
| 7,723,471 | B2 | 5/2010 | Levy et al. |
| 7,825,091 | B2 | 11/2010 | Bloom et al. |
| 8,058,233 | B2 | 11/2011 | Cowley et al. |
| 8,076,288 | B2 | 12/2011 | Levy et al. |
| 8,101,576 | B2 | 1/2012 | Bloom |
| 8,202,836 | B2 | 6/2012 | Moore et al. |
| 8,217,001 | B2 | 7/2012 | Cowley et al. |
| 8,263,736 | B2 | 9/2012 | Bloom |
| 2005/0002927 | A1 | 1/2005 | Quay et al. |
| 2005/0176630 | A1 | 8/2005 | Cowley et al. |
| 2006/0014678 | A1 | 1/2006 | Cowley et al. |
| 2006/0094652 | A1 | 5/2006 | Levy et al. |
| 2006/0094653 | A1 | 5/2006 | Levy et al. |
| 2006/0135747 | A1 | 6/2006 | Levy et al. |
| 2006/0293232 | A1 | 12/2006 | Levy et al. |
| 2009/0209461 | A1 | 8/2009 | Cowley et al. |
| 2009/0215682 | A1 | 8/2009 | Moore et al. |
| 2009/0286723 | A1 | 11/2009 | Levy et al. |
| 2009/0318347 | A1 | 12/2009 | Bloom |
| 2010/0279930 | A1 | 11/2010 | Bloom |
| 2012/0040893 | A1 | 2/2012 | Cowley et al. |
| 2012/0253023 | A1 | 10/2012 | Levy et al. |
| 2013/0023464 | A1 | 1/2013 | Bloom |
| 2013/0303443 | A1 | 11/2013 | BLOOM |

FOREIGN PATENT DOCUMENTS

| | | |
|---|---|---|
| WO | 93/09227 | 5/1993 |
| WO | 95/05848 | 2/1995 |
| WO | 03/026591 | 4/2003 |
| WO | 03/057235 | 7/2003 |
| WO | 2005/077072 | 8/2005 |
| WO | 2005/077094 | 8/2005 |
| WO | 2005/089786 | 9/2005 |
| WO | 2005/089789 | 9/2005 |
| WO | 2005/089790 | 9/2005 |
| WO | 2006/066024 | 6/2006 |
| WO | 2007/008778 | 1/2007 |
| WO | 2007/022123 | 2/2007 |
| WO | 2008/003947 | 10/2008 |
| WO | 2011/092473 | 8/2011 |

OTHER PUBLICATIONS

Batterham et al. "Gut hormone PYY A3-36U physiologically inhibits food intake" *Nature*, vol. 418 pp. 650-654 (Aug. 2002).
Bowie et al. "Deciphering the message in protein sequences: Tolerance to amino acid substitutions" *Science*, vol. 247, No. 4948, pp. 1306-1310 (Mar. 1990).
Druce et al. "Investigation of structure-activity relationships of oxyntomodulin (Oxm) using Oxm analogs" *Endocrinology*, vol. 150, No. 4, pp. 1712-1721 (Apr. 2009).
Dumont et al. "Characterization of a selective neuropeptide Y/peptide YY Y2 receptor radioligand" *Society for Neuroscience Abstracts*, vol. 19, p. 726, abstract 299.8 (Nov. 1993).
Geneseq Database "Human pancreatic polypeptide family peptide SEQ ID No. 44" retrieved from EBI Accession No. GSP: AEJ39513, one page (Sep. 2006).
Morgan et al. "Reduced NPY induced feeding in diabetic but not steroid-treated rats: Lack of evidence for changes in receptor number or affinity" *Journal of Neuroendocrinology*, vol. 8, No. 4, pp. 283-290 (Apr. 1996).
Int'l Search Report for PCT/GB2012/000086, three pages, mailed May 14, 2012.
Written Opinion of PCT/US2010/002099, six pages, mailed May 14, 2012.

*Primary Examiner* — John Ulm
(74) *Attorney, Agent, or Firm* — Nixon & Vanderhye PC

(57) ABSTRACT

Peptide analogs of peptide YY (PYY), compositions comprising them, and methods of using those analogs or compositions for the treatment and prevention of metabolic disorders, for example disorders of energy metabolism such as diabetes and obesity, and for reduction in appetite, reduction in food intake or reduction of calorie intake in a subject, are provided herein.

19 Claims, 4 Drawing Sheets

Xaa$^2$-Ile-His-Pro-His-Ala-Pro-Gly-Glu-Asp-Ala-Ser-Pro-Glu-Glu-Leu-Xaa$^{18}$-His-Tyr-Xaa$^{21}$-Xaa$^{22}$-Xaa$^{23}$-Leu-Xaa$^{25}$-His-Tyr-Leu-Asn-Xaa$^{30}$-Val-Thr-Arg-Gln-Arg-Tyr-NH$_2$

| Analogue No. | SEQ ID NO | Reference | Xaa$^2$ | Xaa$^{18}$ | Xaa$^{21}$ | Xaa$^{22}$ | Xaa$^{23}$ | Xaa$^{25}$ | Xaa$^{30}$ | Binding Ratio | Food Intake Ratio |
|---|---|---|---|---|---|---|---|---|---|---|---|
| 1 | 48 | 4070390 | Pro | Ile | Phe | Ala | Ala | Arg | His | 0.4 | 1.0 |
| 2 | 44 | 4070882 | Pro | Leu | Tyr | Ile | Ala | Arg | Leu | 0.4 | 1.1 |
| 3 | 49 | 4071230 | Pro | Leu | Tyr | Leu | Ala | Arg | Leu | | 0.8 |
| 4 | 50 | 4070391 | Pro | Leu | Phe | Ala | Ala | Arg | His | 0.4 | |
| 5 | 51 | 4070882 | Pro | Leu | Tyr | Val | Val | Arg | Leu | | |
| 6 | 52 | 4071572 | Pro | Leu | Tyr | Ile | Leu | Arg | Leu | | |
| 7 | 53 | 4071573 | Pro | Leu | Tyr | Ile | Ala | Arg | Leu | | |
| 8 | 54 | 4072847 | Pro | Leu | Tyr | Ala | Ala | Arg | Leu | | |
| 9 | 55 | 4072848 | Pro | Leu | Tyr | Ala | Ser | Arg | Leu | | |
| 10 | 56 | 4072849 | Pro | Leu | Tyr | Ile | Ser | Arg | Leu | | |
| 11 | 57 | | Gly | Leu | Tyr | Ile | Ala | Arg | Leu | | |

Figure 1

SEQUENCE LISTING

```
<160> NUMBER OF SEQ ID NOS: 57

<210> SEQ ID NO 1
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
```

```
<221> NAME/KEY: MOD_RES
<222> LOCATION: (35)..(35)
<223> OTHER INFORMATION: AMIDATION

<400> SEQUENCE: 1

Xaa Ile His Pro His Ala Pro Gly Glu Asp Ala Ser Pro Glu Glu Leu
1               5                   10                  15

Xaa His Tyr Xaa Xaa Xaa Leu Xaa His Tyr Leu Asn Xaa Val Thr Arg
            20                  25                  30

Gln Arg Tyr
        35

<210> SEQ ID NO 2
<211> LENGTH: 36
<212> TYPE: PRT
<213> ORGANISM: Homo sapiens

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 34
<212> TYPE: PRT
<213> ORGANISM: Homo sapiens

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 4
<211> LENGTH: 36
<212> TYPE: PRT
<213> ORGANISM: Rattus norvegicus

<400> SEQUENCE: 4

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35

<210> SEQ ID NO 5
<211> LENGTH: 36
<212> TYPE: PRT
<213> ORGANISM: Mus musculus

<400> SEQUENCE: 5

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30
```

Arg Gln Arg Tyr
            35

<210> SEQ ID NO 6
<211> LENGTH: 36
<212> TYPE: PRT
<213> ORGANISM: Sus

<400> SEQUENCE: 6

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
            35

<210> SEQ ID NO 7
<211> LENGTH: 36
<212> TYPE: PRT
<213> ORGANISM: Cavia porcellus

<400> SEQUENCE: 7

Tyr Pro Ser Lys Pro Glu Ala Pro Gly Ser Asp Ala Ser Pro Glu Glu
1               5                   10                  15

Leu Ala Arg Tyr Tyr Ala Ser Leu Arg His Tyr Leu Asn Leu Val Thr
            20                  25                  30

Arg Gln Arg Tyr
            35

<210> SEQ ID NO 8
<211> LENGTH: 36
<212> TYPE: PRT
<213> ORGANISM: Anura

<400> SEQUENCE: 8

Tyr Pro Pro Lys Pro Glu Asn Pro Gly Glu Asp Ala Ser Pro Glu Glu
1               5                   10                  15

Met Thr Lys Tyr Leu Thr Ala Leu Arg His Tyr Ile Asn Leu Val Thr
            20                  25                  30

Arg Gln Arg Tyr
            35

<210> SEQ ID NO 9
<211> LENGTH: 36
<212> TYPE: PRT
<213> ORGANISM: Raja

<400> SEQUENCE: 9

Tyr Pro Pro Lys Pro Glu Asn Pro Gly Asp Asp Ala Ala Pro Glu Glu
1               5                   10                  15

Leu Ala Lys Tyr Tyr Ser Ala Leu Arg His Tyr Ile Asn Leu Ile Thr
            20                  25                  30

Arg Gln Arg Tyr
            35

<210> SEQ ID NO 10
<211> LENGTH: 36
<212> TYPE: PRT
<213> ORGANISM: Squaliformes

<400> SEQUENCE: 10

Tyr Pro Pro Lys Pro Glu Asn Pro Gly Glu Asp Ala Pro Pro Glu
1               5                   10                  15

Leu Ala Lys Tyr Tyr Ser Ala Leu Arg His Tyr Ile Asn Leu Ile Thr
                20                  25                  30

Arg Gln Arg Tyr
            35

<210> SEQ ID NO 11
<211> LENGTH: 36
<212> TYPE: PRT
<213> ORGANISM: Lampetra

<400> SEQUENCE: 11

Phe Pro Pro Lys Pro Asp Asn Pro Gly Asp Asn Ala Ser Pro Glu Gln
1               5                   10                  15

Met Ala Arg Tyr Lys Ala Ala Val Arg His Tyr Ile Asn Leu Ile Thr
                20                  25                  30

Arg Gln Arg Tyr
            35

<210> SEQ ID NO 12
<211> LENGTH: 36
<212> TYPE: PRT
<213> ORGANISM: Petromyzon

<400> SEQUENCE: 12

Met Pro Pro Lys Pro Asp Asn Pro Ser Pro Asp Ala Ser Pro Glu Glu
1               5                   10                  15

Leu Ser Lys Tyr Met Leu Ala Val Arg Asn Tyr Ile Asn Leu Ile Thr
                20                  25                  30

Arg Gln Arg Tyr
            35

<210> SEQ ID NO 13
<211> LENGTH: 36
<212> TYPE: PRT
<213> ORGANISM: Canis familiaris

<400> SEQUENCE: 13

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
                20                  25                  30

Arg Gln Arg Tyr
            35

<210> SEQ ID NO 14
<211> LENGTH: 36
<212> TYPE: PRT
<213> ORGANISM: Macaca mulatta

<400> SEQUENCE: 14

Tyr Pro Ile Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
                20                  25                  30

Arg Gln Arg Tyr
            35

<210> SEQ ID NO 15

```
<211> LENGTH: 36
<212> TYPE: PRT
<213> ORGANISM: Xenopus tropicalis

<400> SEQUENCE: 15

Tyr Pro Thr Lys Pro Glu Asn Pro Gly Asn Asp Ala Ser Pro Glu Glu
1               5                   10                  15

Met Ala Lys Tyr Leu Thr Ala Leu Arg His Tyr Ile Asn Leu Val Thr
                20                  25                  30

Arg Gln Arg Tyr
            35

<210> SEQ ID NO 16
<211> LENGTH: 36
<212> TYPE: PRT
<213> ORGANISM: Salmo salar

<400> SEQUENCE: 16

Tyr Pro Pro Lys Pro Glu Asn Pro Gly Glu Asp Ala Pro Pro Glu Glu
1               5                   10                  15

Leu Ala Lys Tyr Tyr Thr Ala Leu Arg His Tyr Ile Asn Leu Ile Thr
                20                  25                  30

Arg Gln Arg Tyr
            35

<210> SEQ ID NO 17
<211> LENGTH: 36
<212> TYPE: PRT
<213> ORGANISM: Bos taurus

<400> SEQUENCE: 17

Tyr Pro Ala Lys Pro Gln Ala Pro Gly Glu His Ala Ser Pro Asp Glu
1               5                   10                  15

Leu Asn Arg Tyr Tyr Thr Ser Leu Arg His Tyr Leu Asn Leu Val Thr
                20                  25                  30

Arg Gln Arg Phe
            35

<210> SEQ ID NO 18
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
```

<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 18

Pro Ile His Pro His Ala Pro Gly Glu Asp Ala Ser Pro Glu Glu Leu
1               5                   10                  15

Xaa His Tyr Xaa Xaa Xaa Leu Xaa His Tyr Leu Asn Xaa Val Thr Arg
            20                  25                  30

Gln Arg Tyr
        35

<210> SEQ ID NO 19
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 19

Gly Ile His Pro His Ala Pro Gly Glu Asp Ala Ser Pro Glu Glu Leu
1               5                   10                  15

Xaa His Tyr Xaa Xaa Xaa Leu Xaa His Tyr Leu Asn Xaa Val Thr Arg
            20                  25                  30

Gln Arg Tyr
        35

<210> SEQ ID NO 20
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu or Ile

```
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 20

Xaa Ile His Pro His Ala Pro Gly Glu Asp Ala Ser Pro Glu Glu Leu
1               5                   10                  15

Xaa His Tyr Xaa Xaa Xaa Leu Xaa His Tyr Leu Asn Xaa Val Thr Arg
            20                  25                  30

Gln Arg Tyr
        35

<210> SEQ ID NO 21
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 21

Xaa Ile His Pro His Ala Pro Gly Glu Asp Ala Ser Pro Glu Glu Leu
1               5                   10                  15

Leu His Tyr Xaa Xaa Xaa Leu Xaa His Tyr Leu Asn Xaa Val Thr Arg
            20                  25                  30
```

Gln Arg Tyr
        35

<210> SEQ ID NO 22
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 22

Xaa Ile His Pro His Ala Pro Gly Glu Asp Ala Ser Pro Glu Glu Leu
1               5                   10                  15

Xaa His Tyr Phe Xaa Xaa Leu Xaa His Tyr Leu Asn Xaa Val Thr Arg
            20                  25                  30

Gln Arg Tyr
        35

<210> SEQ ID NO 23
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:

```
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 23

Xaa Ile His Pro His Ala Pro Gly Glu Asp Ala Ser Pro Glu Glu Leu
1               5                   10                  15

Xaa His Tyr Tyr Xaa Xaa Leu Xaa His Tyr Leu Asn Xaa Val Thr Arg
            20                  25                  30

Gln Arg Tyr
        35

<210> SEQ ID NO 24
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 24

Xaa Ile His Pro His Ala Pro Gly Glu Asp Ala Ser Pro Glu Glu Leu
1               5                   10                  15

Xaa His Tyr Xaa Xaa Xaa Leu Xaa His Tyr Leu Asn Xaa Val Thr Arg
            20                  25                  30

Gln Arg Tyr
        35

<210> SEQ ID NO 25
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
```

```
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 25

Xaa Ile His Pro His Ala Pro Gly Glu Asp Ala Ser Pro Glu Glu Leu
 1               5                  10                  15

Xaa His Tyr Xaa Leu Xaa Leu Xaa His Tyr Leu Asn Xaa Val Thr Arg
            20                  25                  30

Gln Arg Tyr
        35

<210> SEQ ID NO 26
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 26

Xaa Ile His Pro His Ala Pro Gly Glu Asp Ala Ser Pro Glu Glu Leu
 1               5                  10                  15
```

```
Xaa His Tyr Xaa Ile Xaa Leu Xaa His Tyr Leu Asn Xaa Val Thr Arg
            20                  25                  30

Gln Arg Tyr
        35
```

<210> SEQ ID NO 27
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 27

```
Xaa Ile His Pro His Ala Pro Gly Glu Asp Ala Ser Pro Glu Glu Leu
1               5                   10                  15

Xaa His Tyr Xaa Xaa Ala Leu Xaa His Tyr Leu Asn Xaa Val Thr Arg
            20                  25                  30

Gln Arg Tyr
        35
```

<210> SEQ ID NO 28
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)

```
<223> OTHER INFORMATION: Xaa is Ala, Leu, Gly, Val or Ser
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 28

Xaa Ile His Pro His Ala Pro Gly Glu Asp Ala Ser Pro Glu Glu Leu
 1               5                  10                  15

Xaa His Tyr Xaa Xaa Xaa Leu Arg His Tyr Leu Asn Xaa Val Thr Arg
            20                  25                  30

Gln Arg Tyr
        35

<210> SEQ ID NO 29
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 29

Xaa Ile His Pro His Ala Pro Gly Glu Asp Ala Ser Pro Glu Glu Leu
 1               5                  10                  15

Xaa His Tyr Xaa Xaa Xaa Leu His His Tyr Leu Asn Xaa Val Thr Arg
            20                  25                  30

Gln Arg Tyr
        35

<210> SEQ ID NO 30
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
```

```
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: MOD_RES
<222> LOCATION: (35)..(35)
<223> OTHER INFORMATION: AMIDATION

<400> SEQUENCE: 30

Xaa Ile His Pro His Ala Pro Gly Glu Asp Ala Ser Pro Glu Glu Leu
 1               5                  10                  15

Xaa His Tyr Xaa Xaa Xaa Leu Xaa His Tyr Leu Asn His Val Thr Arg
            20                  25                  30

Gln Arg Tyr
        35

<210> SEQ ID NO 31
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile, Leu, Ala or Val
<220> FEATURE:
<221> NAME/KEY: misc_feature
<222> LOCATION: (22)..(22)
<223> OTHER INFORMATION: Xaa is Ala, Leu, Gly, Val or Ser
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: MOD_RES
<222> LOCATION: (35)..(35)
<223> OTHER INFORMATION: AMIDATION

<400> SEQUENCE: 31

Xaa Ile His Pro His Ala Pro Gly Glu Asp Ala Ser Pro Glu Glu Leu
 1               5                  10                  15

Xaa His Tyr Xaa Xaa Xaa Leu Xaa His Tyr Leu Asn Leu Val Thr Arg
            20                  25                  30
```

Gln Arg Tyr
        35

<210> SEQ ID NO 32
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 32

Pro Ile His Pro His Ala Pro Gly Glu Asp Ala Ser Pro Glu Glu Leu
1               5                   10                  15

Xaa His Tyr Xaa Xaa Ala Leu Xaa His Tyr Leu Asn Xaa Val Thr Arg
            20                  25                  30

Gln Arg Tyr
        35

<210> SEQ ID NO 33
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (1)..(1)
<223> OTHER INFORMATION: Xaa is Pro or Gly
<220> FEATURE:
<221> NAME/KEY: misc_feature
<222> LOCATION: (17)..(17)
<223> OTHER INFORMATION: Xaa is Leu or Ile
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION -continued

<400> SEQUENCE: 33

Xaa Ile His Pro His Ala Pro Gly Glu Asp Ala Ser Pro Glu Glu Leu
1               5                   10                  15

Xaa His Tyr Tyr Xaa Ala Leu Xaa His Tyr Leu Asn Xaa Val Thr Arg
            20                  25                  30

Gln Arg Tyr
        35

<210> SEQ ID NO 34
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 34

Pro Ile His Pro His Ala Pro Gly Glu Asp Ala Ser Pro Glu Glu Leu
1               5                   10                  15

Xaa His Tyr Tyr Xaa Ala Leu Xaa His Tyr Leu Asn Xaa Val Thr Arg
            20                  25                  30

Gln Arg Tyr
        35

<210> SEQ ID NO 35
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 35

Pro Ile His Pro His Ala Pro Gly Glu Asp Ala Ser Pro Glu Glu Leu
1               5                   10                  15

Xaa His Tyr Tyr Xaa Ala Leu Arg His Tyr Leu Asn Xaa Val Thr Arg
            20                  25                  30

Gln Arg Tyr
        35

<210> SEQ ID NO 36
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: misc_feature
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 36

Pro Ile His Pro His Ala Pro Gly Glu Asp Ala Ser Pro Glu Glu Leu
1               5                   10                  15

Leu His Tyr Tyr Xaa Ala Leu Arg His Tyr Leu Asn Xaa Val Thr Arg
            20                  25                  30

Gln Arg Tyr
        35

<210> SEQ ID NO 37
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: MOD_RES
<222> LOCATION: (35)..(35)
<223> OTHER INFORMATION: AMIDATION

<400> SEQUENCE: 37

Pro Ile His Pro His Ala Pro Gly Glu Asp Ala Ser Pro Glu Glu Leu
1               5                   10                  15

Leu His Tyr Tyr Xaa Ala Leu Arg His Tyr Leu Asn Leu Val Thr Arg
            20                  25                  30

Gln Arg Tyr
        35

<210> SEQ ID NO 38
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: MOD_RES
<222> LOCATION: (35)..(35)
<223> OTHER INFORMATION: AMIDATION -continued

<400> SEQUENCE: 38

Pro Ile His Pro His Ala Pro Gly Glu Asp Ala Ser Pro Glu Glu Leu
1               5                   10                  15

Leu His Tyr Tyr Xaa Ala Leu Arg His Tyr Leu Asn His Val Thr Arg
            20                  25                  30

Gln Arg Tyr
        35

<210> SEQ ID NO 39
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: MOD_RES
<222> LOCATION: (35)..(35)
<223> OTHER INFORMATION: AMIDATION

<400> SEQUENCE: 39

Pro Ile His Pro His Ala Pro Gly Glu Asp Ala Ser Pro Glu Glu Leu
1               5                   10                  15

Xaa His Tyr Xaa Xaa Ala Leu Xaa His Tyr Leu Asn Leu Val Thr Arg
            20                  25                  30

Gln Arg Tyr
        35

<210> SEQ ID NO 40
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: misc_feature
<222> LOCATION: (24)..(24)
<223> OTHER INFORMATION: Xaa is Arg or His
<220> FEATURE:
<221> NAME/KEY: MOD_RES
<222> LOCATION: (35)..(35)
<223> OTHER INFORMATION: AMIDATION

<400> SEQUENCE: 40

Pro Ile His Pro His Ala Pro Gly Glu Asp Ala Ser Pro Glu Glu Leu
1               5                   10                  15

Xaa His Tyr Xaa Xaa Ala Leu Xaa His Tyr Leu Asn His Val Thr Arg
            20                  25                  30

Gln Arg Tyr
        35

<210> SEQ ID NO 41
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: MOD_RES
<222> LOCATION: (35)..(35)
<223> OTHER INFORMATION: AMIDATION

<400> SEQUENCE: 41

Pro Ile His Pro His Ala Pro Gly Glu Asp Ala Ser Pro Glu Glu Leu
1               5                   10                  15

Xaa His Tyr Xaa Xaa Ala Leu Arg His Tyr Leu Asn Leu Val Thr Arg
            20                  25                  30

Gln Arg Tyr
        35

<210> SEQ ID NO 42
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile or Leu
<220> FEATURE:
<221> NAME/KEY: MOD_RES
<222> LOCATION: (35)..(35)
<223> OTHER INFORMATION: AMIDATION

<400> SEQUENCE: 42

Pro Ile His Pro His Ala Pro Gly Glu Asp Ala Ser Pro Glu Glu Leu
1               5                   10                  15

Xaa His Tyr Xaa Xaa Ala Leu Arg His Tyr Leu Asn His Val Thr Arg
            20                  25                  30

Gln Arg Tyr

```
<210> SEQ ID NO 43
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: misc_feature
<222> LOCATION: (17)..(17)
<223> OTHER INFORMATION: Xaa is Leu, Ile or Lys
<220> FEATURE:
<221> NAME/KEY: misc_feature
<222> LOCATION: (20)..(20)
<223> OTHER INFORMATION: Xaa is Tyr or Phe
<220> FEATURE:
<221> NAME/KEY: misc_feature
<222> LOCATION: (21)..(21)
<223> OTHER INFORMATION: Xaa is Ile or Ala
<220> FEATURE:
<221> NAME/KEY: MOD_RES
<222> LOCATION: (35)..(35)
<223> OTHER INFORMATION: AMIDATION

<400> SEQUENCE: 43

Pro Ile His Pro His Ala Pro Gly Glu Asp Ala Ser Pro Glu Glu Leu
1               5                   10                  15

Xaa His Tyr Xaa Xaa Ala Leu Arg His Tyr Leu Asn His Val Thr Arg
            20                  25                  30

Gln Arg Tyr
        35

<210> SEQ ID NO 44
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 44

Pro Ile His Pro His Ala Pro Gly Glu Asp Ala Ser Pro Glu Glu Leu
1               5                   10                  15

Leu His Tyr Tyr Ile Ala Leu Arg His Tyr Leu Asn Leu Val Thr Arg
            20                  25                  30

Gln Arg Tyr
        35

<210> SEQ ID NO 45
<211> LENGTH: 5
<212> TYPE: PRT
<213> ORGANISM: Artificial Sequence
<220> FEATURE:
<223> OTHER INFORMATION: cleavable linker peptide

<400> SEQUENCE: 45

Asp Asp Asp Asp Tyr
1               5

<210> SEQ ID NO 46
<211> LENGTH: 5
<212> TYPE: PRT
<213> ORGANISM: Artificial Sequence
<220> FEATURE:
```

<223> OTHER INFORMATION: cleavable linker peptide

<400> SEQUENCE: 46

His Pro Phe His Leu
1               5

<210> SEQ ID NO 47
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MISC_FEATURE
<222> LOCATION: (21)..(21)
<223> OTHER INFORMATION: Xaa is Ile or Leu
<220> FEATURE:
<221> NAME/KEY: MISC_FEATURE
<222> LOCATION: (24)..(24)
<223> OTHER INFORMATION: Xaa is Arg or His
<220> FEATURE:
<221> NAME/KEY: MISC_FEATURE
<222> LOCATION: (29)..(29)
<223> OTHER INFORMATION: Xaa is Leu or His
<220> FEATURE:
<221> NAME/KEY: MOD_RES
<222> LOCATION: (35)..(35)
<223> OTHER INFORMATION: AMIDATION

<400> SEQUENCE: 47

Pro Ile His Pro His Ala Pro Gly Glu Asp Ala Ser Pro Glu Glu Leu
1               5                   10                  15

Leu His Tyr Tyr Xaa Ala Leu Xaa His Tyr Leu Asn Xaa Val Thr Arg
            20                  25                  30

Gln Arg Tyr
        35

<210> SEQ ID NO 48
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 48

Pro Ile His Pro His Ala Pro Gly Glu Asp Ala Ser Pro Glu Glu Leu
1               5                   10                  15

Ile His Tyr Phe Ala Ala Leu Arg His Tyr Leu Asn His Val Thr Arg
            20                  25                  30

Gln Arg Tyr
        35

<210> SEQ ID NO 49
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 49

```
Pro Ile His Pro His Ala Pro Gly Glu Asp Ala Ser Pro Glu Glu Leu
1               5                   10                  15

Leu His Tyr Tyr Leu Ala Leu Arg His Tyr Leu Asn Leu Val Thr Arg
            20                  25                  30

Gln Arg Tyr
        35

<210> SEQ ID NO 50
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 50

Pro Ile His Pro His Ala Pro Gly Glu Asp Ala Ser Pro Glu Glu Leu
1               5                   10                  15

Leu His Tyr Phe Ala Ala Leu Arg His Tyr Leu Asn His Val Thr Arg
            20                  25                  30

Gln Arg Tyr
        35

<210> SEQ ID NO 51
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 51

Pro Ile His Pro His Ala Pro Gly Glu Asp Ala Ser Pro Glu Glu Leu
1               5                   10                  15

Leu His Tyr Tyr Val Ala Leu Arg His Tyr Leu Asn Leu Val Thr Arg
            20                  25                  30

Gln Arg Tyr
        35

<210> SEQ ID NO 52
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 52

Pro Ile His Pro His Ala Pro Gly Glu Asp Ala Ser Pro Glu Glu Leu
1               5                   10                  15

Leu His Tyr Tyr Ile Val Leu Arg His Tyr Leu Asn Leu Val Thr Arg
            20                  25                  30

Gln Arg Tyr
        35
```

```
<210> SEQ ID NO 53
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 53

Pro Ile His Pro His Ala Pro Gly Glu Asp Ala Ser Pro Glu Glu Leu
1               5                   10                  15

Leu His Tyr Tyr Ile Leu Leu Arg His Tyr Leu Asn Leu Val Thr Arg
            20                  25                  30

Gln Arg Tyr
        35

<210> SEQ ID NO 54
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 54

Pro Ile His Pro His Ala Pro Gly Glu Asp Ala Ser Pro Glu Glu Leu
1               5                   10                  15

Leu His Tyr Tyr Ala Ala Leu Arg His Tyr Leu Asn Leu Val Thr Arg
            20                  25                  30

Gln Arg Tyr
        35

<210> SEQ ID NO 55
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 55

Pro Ile His Pro His Ala Pro Gly Glu Asp Ala Ser Pro Glu Glu Leu
1               5                   10                  15

Leu His Tyr Tyr Ala Ser Leu Arg His Tyr Leu Asn Leu Val Thr Arg
            20                  25                  30

Gln Arg Tyr
        35

<210> SEQ ID NO 56
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION
```

```
<400> SEQUENCE: 56

Pro Ile His Pro His Ala Pro Gly Glu Asp Ala Ser Pro Glu Glu Leu
1               5                   10                  15

Leu His Tyr Tyr Ile Ser Leu Arg His Tyr Leu Asn Leu Val Thr Arg
                20                  25                  30

Gln Arg Tyr
        35

<210> SEQ ID NO 57
<211> LENGTH: 35
<212> TYPE: PRT
<213> ORGANISM: Artificial Sequence
<220> FEATURE:
<223> OTHER INFORMATION: PYY analogue peptide
<220> FEATURE:
<221> NAME/KEY: MOD_RES
<222> LOCATION: (35)..(35)
<223> OTHER INFORMATION: AMIDATION

<400> SEQUENCE: 57

Gly Ile His Pro His Ala Pro Gly Glu Asp Ala Ser Pro Glu Glu Leu
1               5                   10                  15

Leu His Tyr Tyr Ile Ala Leu Arg His Tyr Leu Asn Leu Val Thr Arg
                20                  25                  30

Gln Arg Tyr
        35
```

COMPOUNDS AND THEIR EFFECTS ON FEEDING BEHAVIOUR

This application is the U.S. national phase under 35 U.S.C. 371 of Application No. PCT/GB2012/000086, filed 27 Jan. 2012, which designated the U.S. and claims priority to GB Application No. 1101459.4, filed 27 Jan. 2011; the entire contents of each of which are hereby incorporated by reference.

1. FIELD OF THE INVENTION

This application relates to the use of agents to control appetite, feeding, food intake, energy expenditure and calorie intake, particularly in the field of obesity.

2. BACKGROUND OF THE INVENTION

According to the National Health and Nutrition Examination Survey (NHANES III, 1988 to 1994), between one third and one half of men and women in the United States are overweight. In the United States, sixty percent of men and fifty-one percent of women, of the age of 20 or older, are either overweight or obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type 2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347: 358, 2002). In addition, there is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia.

Although diet and exercise provide a simple process to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have serious adverse side effects. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example, in the upper part of the recommended range, may wish to reduce their weight, to bring it closer to the ideal weight. Thus, a need remains for agents that can be used to effect weight loss in overweight and obese subjects.

In WO03/026591, it is disclosed that peripheral administration of peptide YY (hereinafter PYY), or an agonist thereof, to a subject results in decreased food intake, caloric intake, and appetite, and an alteration in energy metabolism. It is disclosed that the PYY or agonist thereof is preferably an N-terminally deleted PYY molecule PYY 3-36 $NH_2$.

The present invention is based on the discovery that analogues of PYY in which specific amino acid residues are deleted and/or substituted can also be administered to a subject in order to cause decreased food intake, decreased caloric intake, decreased appetite and an alteration in energy metabolism. In many cases the analogues of the present invention exhibit improved potency and/or longer duration of action and/or fewer side effects than native PYY.

3. SUMMARY OF THE INVENTION

According to a first aspect of the invention there is provided an analogue of PYY comprising an amino acid sequence represented by formula (I)

(I)
[SEQ ID NO: 1]
$Xaa^2$-Ile-His-Pro-His-Ala-Pro-Gly-Glu-Asp-Ala-Ser-

Pro-Glu-Glu-Leu-$Xaa^{18}$-His-Tyr-$Xaa^{21}$-$Xaa^{22}$-$Xaa^{23}$-

Leu-$Xaa^{25}$-His-Tyr-Leu-Asn-$Xaa^{30}$-Val-Thr-Arg-Gln-

Arg-Tyr-$NH_2$ wherein
$Xaa^2$ is selected from the group consisting of Pro and Gly;
$Xaa^{18}$ is selected from the group consisting of Leu, Ile and Lys;
$Xaa^{21}$ is selected from the group consisting of Tyr and Phe;
$Xaa^{22}$ is selected from the group consisting of Ile, Leu, Ala and Val;
$Xaa^{23}$ is selected from the group consisting of Ala, Leu, Gly, Val and Ser;
$Xaa^{25}$ is selected from the group consisting of Arg and His; and
$Xaa^{30}$ is selected from the group consisting of Leu and His;
or a compound that is a variant and/or derivative thereof; or a salt thereof, including a salt of such a variant and/or derivative,
a variant being an amino acid sequence having up to two amino acids other than $Xaa^2$, $Xaa^{18}$, $Xaa^{21}$, $Xaa^{22}$, $Xaa^{23}$, $Xaa^{25}$ and $Xaa^{30}$ replaced with a different amino acid.

According to a further aspect of the invention, there is provided an analogue of PYY according to the invention for use as a medicament.

According to a further aspect of the invention, there is provided a pharmaceutical composition comprising an analogue of PYY according to the invention together with a pharmaceutically acceptable carrier and optionally other therapeutic ingredients.

According to a further aspect of the invention, there is provided an analogue of PYY according to the invention, or a pharmaceutical composition comprising an analogue of PYY according to the invention, for use in the treatment of a metabolic disorder.

According to another aspect of the invention, there is provided an analogue of PYY according to the invention, or a pharmaceutical composition comprising an analogue of PYY according to the invention, for use in the reduction of appetite in a subject, for use in the reduction of food intake in a subject, or for use in the reduction of calorie intake in a subject.

According to a further aspect of the invention, there is provided a method for treating a disease or disorder or other non-desired physiological state comprising subcutaneous administration of an analogue of PYY according to the invention, or a pharmaceutical composition comprising an analogue of PYY according to the invention.

According to the invention there is further provided a method for treating a metabolic disorder in the subject in need thereof comprising administering to the subject an analogue of PYY according to the invention, or a pharmaceutical composition comprising an analogue of PYY according to the invention.

There is further provided use of an analogue of PYY according to the invention for the manufacture of a medicament for the treatment of a metabolic disorder.

There is further provided use of an analogue of PYY according to the invention for the manufacture of a medicament for the reduction of appetite in a subject, for the reduction of food intake in a subject, or for the reduction of calorie intake in a subject.

4. BRIEF DESCRIPTION OF THE DRAWINGS

FIG. 1 shows the amino acid sequence $Xaa^2$-Ile-His-Pro-His-Pro-Gly-Glu-Asp-Ala-Ser-Pro-Glu-Glu-Leu-$Xaa^{18}$-His-Tyr-$Xaa^{21}$-$Xaa^{22}$-$Xaa^{23}$-Leu-$Xaa^{25}$-His-Tyr-Leu-Asn-$Xaa^{30}$-Val-Thr-Arg-Gln-Arg-Tyr-$NH_2$ [SEQ ID NO: 1] of PYY analogues of the invention (analogues numbers 1 to 11), the results of binding experiments with those PYY analogues, and the results of experiments in which the appetite suppressant effects in mice of those PYY analogues of the invention have been compared with native PYY 3-36 NH2 as described in Example 1.

5. SEQUENCE LISTING

Figure 2:
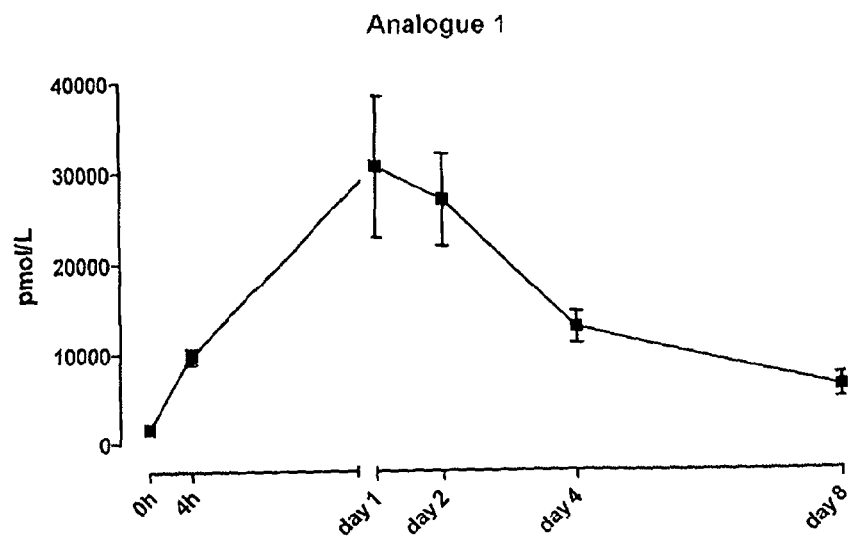
FIGS. 2, 3 and 4 show the results of rat pharmacokinetic studies described in Example 2.

The amino acid sequences listed in the application are shown using standard letter abbreviations for amino acids. The specific sequences given herein relate to specific preferred embodiments of the invention.

6. DEFINITIONS

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Appetite: A natural desire, or longing for food. In one embodiment, appetite is measured by a survey to assess the desire for food. Increased appetite generally leads to increased feeding behavior.

Appetite Suppressants: Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by $height^2$ (in $meters^2$). The current standards for both men and women accepted as "normal" are a BMI of 20-24.9 $kg/m^2$. In one embodiment, a BMI of greater than 25 $kg/m^2$ can be used to identify an obese subject. Grade I obesity corresponds to a BMI of 25-29.9 $kg/m^2$. Grade II obesity corresponds to a BMI of 30-40 $kg/m^2$; and Grade III obesity corresponds to a BMI greater than 40 $kg/m^2$ (Jequier, *Am. J. Clin. Nutr.* 45:1035-47, 1987). Ideal body weight will vary among species and individuals based on height, body build, bone structure, and sex.

Conservative Substitutions: The replacement of an amino acid residue by another, biologically similar residue in a polypeptide. The term "conservative variation" also includes the use of a substituted amino acid, i.e. an amino with one or more atoms replaced with another atom or group, in place of a parent amino acid provided that antibodies raised to the substituted polypeptide also immunoreact with the unsubstituted polypeptide.

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of β cells, which results in insufficient levels of endogenous insulin. Diabetes type II, or non-insulin dependent diabetes, results from a defect in both the body's sensitivity to insulin, and a relative deficiency in insulin production.

Food Intake: The amount of food consumed by an individual. Food intake can be measured by volume or by weight. For example, food intake may be the total amount of food consumed by an individual. Or, food intake may be the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

Hyperpolarization: A decrease in the membrane potential of a cell. Inhibitory neurotransmitters inhibit the transmission of nerve impulses via hyperpolarization. This hyperpolarization is called an inhibitory postsynaptic potential (IPSP). Although the threshold voltage of the cell is uncharged, a hyperpolarized cell requires a stronger excitatory stimulus to reach threshold.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102: E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 kg/m$^2$ to 29.9 kg/m$^2$ is overweight, while a BMI of 30 kg/m$^2$ or greater is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fain. Phys.* 63:2185, 2001).

Overweight: An individual who weighs more than their ideal body weight. An overweight individual can be obese, but is not necessarily obese. For example, an overweight individual is any individual who desires to decrease their weight. In one convention, an overweight individual is an individual with a BMI of 25.0 kg/m$^2$ to 29.9 kg/m$^2$ Pegylated and Pegylation: the process of reacting a poly (alkylene glycol), preferably an activated poly(alkylene glycol) to form a covalent bond. A facilitator may be used, for example an amino acid, e.g. lysine. Although "pegylation" is often carried out using poly(ethylene glycol) or derivatives thereof, such as methoxy poly(ethylene glycol), the term is not limited herein to the use of methoxy poly(ethylene glycol) but also includes the use of any other useful poly(alkylene glycol), for example poly(propylene glycol).

pI: pI is an abbreviation for isoelectric point. An alternative abbreviation sometimes used is IEP. It is the pH at which a particular molecule carries no net electric charge. At a pH below its pI a protein or peptide carries a net positive charge. At a pH above its pI a protein or peptide carries a net negative charge. Proteins and peptides can be separated according to their isoelectric points using a technique called isoelectric focussing which is an electrophoretic method that utilises a pH gradient contained within a polyacrylimide gel.

Peptide YY (PYY): The term PYY as used herein refers to a peptide YY polypeptide, a hormone secreted into the blood by cells lining the lower small intestine (the ileum) and the colon. Naturally occurring wild type PYY sequences for various species are shown in Table 1.

TABLE 1

PYY sequence of various species

| PEPTIDE YY | AA SEQUENCE |
| --- | --- |
| Human | YPIKPEAPGEDASPEELNRYYASLRHYLNLVTRQRY [SEQ ID NO: 2] |
| Human 3-36 | IKPEAPGEDASPEELNRYYASLRHYLNLVTRQRY [SEQ ID NO: 3] |
| Rat (*Rattus norvegicus*) | YPAKPEAPGEDASPEELSRYYASLRHYLNLVTRQRY [SEQ ID NO: 4] |
| Mouse (*Mus musculus*) | YPAKPEAPGEDASPEELSRYYASLRHYLNLVTRQRY [SEQ ID NO: 5] |
| Pig | YPAKPEAPGEDASPEELSRYYASLRHYLNLVTRQRY [SEQ ID NO: 6] |
| Guinea pig | YPSKPEAPGSDASPEELARYYASLRHYLNLVTRQRY [SEQ ID NO: 7] |
| Frog | YPPKPENPGEDASPEEMTKYLTALRHYINLVTRQRY [SEQ ID NO: 8] |
| Raja | YPPKPENPGDDAAPEELAKYYSALRHYINLITRQRY [SEQ ID NO: 9] |
| Dogfish | YPPKPENPGEDAPPEELAKYYSALRHYINLITRQRY [SEQ ID NO: 10] |
| Lampetra | FPPKPDNPGDNASPEQMARYKAAVRHYINLITRQRY [SEQ ID NO: 11] |
| Petromyzon | MPPKPDNPSPDASPEELSKYMLAVRNYINLITRQRY [SEQ ID NO: 12] |
| Dog (*Canis familiaris*) | YPAKPEAPGEDASPEELSRYYASLRHYLNLVTRQRY [SEQ ID NO: 13] |
| Rhesus monkey (*Macaca mulatta*) | YPIKPEAPGEDASPEELSRYYASLRHYLNLVTRQRY [SEQ ID NO: 14] |
| Pipid frog (*Xenopus tropicalis*) | YPTKPENPGNDASPEEMAKYLTALRHYINLVTRQRY [SEQ ID NO: 15] |
| Atlantic salmon (*Salmo salar*) | YPPKPENPGEDAPPEELAKYYTALRHYINLITRQRY [SEQ ID NO: 16] |
| Cattle (*bos taurus*) | YPAKPQAPGEHASPDELNRYYTSLRHYLNLVTRQRF [SEQ ID NO: 17] |

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein encompass any amino acid sequence and include modified sequences such as glycoproteins. The term "polypeptide" is specifically covers naturally occurring proteins, as well as those which are recombinantly or synthetically produced. The term "polypeptide fragment" refers to a portion of a polypeptide, for example a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Subcutaneous Administration: Subcutaneous administration is administration of a substance to the subcutaneous layer of fat which is found between the dermis of the skin and the underlying tissue. Subcutaneous administration may be by an injection using a hypodermic needle fitted, for example, to a syringe or a "pen" type injection device. Other administration methods may be used for example microneedles. Injection with a hypodermic needle typically involves a degree of pain on behalf of the recipient. Such pain may be masked by use of a local anaesthetic or analgesic. However, the usual method used to reduce the perceived pain of injections is to merely distract the subject immediately prior to and during the injection. Pain may be minimised by using a relatively small gauge hypodermic needle, by injecting a relatively small volume of substance and by avoiding excessively acidic or alkali compositions which may cause the subject to experience a "stinging" sensation at the injection site. Compositions having a pH of between pH4 and pH10 are usually regarded as tolerably comfortable.

Therapeutically Effective Amount: A dose sufficient to prevent advancement, or to cause regression of a disorder, or which is capable of relieving a sign or symptom of a disorder, or which is capable of achieving a desired result. In several embodiments, a therapeutically effective amount of a compound of the invention is an amount sufficient to inhibit or halt weight gain, or an amount sufficient to decrease appetite, or an amount sufficient to reduce caloric intake or food intake or increase energy expenditure.

7. DETAILED DESCRIPTION

According to a first aspect of the invention there is provided an analogue of PYY comprising an amino acid sequence represented by formula (I)

(I)
[SEQ ID NO: 1]
Xaa$^2$-Ile-His-Pro-His-Ala-Pro-Gly-Glu-Asp-Ala-Ser-

Pro-Glu-Glu-Leu-Xaa$^{18}$-His-Tyr-Xaa$^{21}$-Xaa$^{22}$-Xaa$^{23}$-

-continued
Leu-Xaa$^{25}$-His-Tyr-Leu-Asn-Xaa$^{30}$-Val-Thr-Arg-Gln-

Arg-Tyr-NH$_2$ wherein
  Xaa$^2$ is selected from the group consisting of Pro and Gly;
  Xaa$^{18}$ is selected from the group consisting of Leu, Ile and Lys;
  Xaa$^{21}$ is selected from the group consisting of Tyr and Phe;
  Xaa$^{22}$ is selected from the group consisting of Ile, Leu, Ala and Val;
  Xaa$^{23}$ is selected from the group consisting of Ala, Leu, Gly, Val and Ser;
  Xaa$^{25}$ is selected from the group consisting of Arg and His; and
  Xaa$^{30}$ is selected from the group consisting of Leu and His;
or a compound that is a variant and/or derivative thereof; or a salt thereof, including a salt of such a variant and/or derivative,
a variant being an amino acid sequence having up to two amino acids other than Xaa$^2$, Xaa$^{18}$, Xaa$^{21}$, Xaa$^{22}$, Xaa$^{23}$, Xaa$^{25}$ and Xaa$^{30}$ replaced with a different amino acid.

The PYY analogues of the invention comprise a sequence in which Xaa$^2$ is Pro or Gly. According to certain embodiments Xaa$^2$ is Pro [SEQ ID NO: 18]. According to other embodiments Xaa$^2$ is Gly [SEQ ID NO: 19].

Xaa$^{18}$ is selected from the group consisting of Leu, Lys and Ile. Preferably, Xaa$^{18}$ is selected from the group consisting of Leu and Ile [SEQ ID NO: 20]. In some embodiments, Xaa$^{18}$ is Leu [SEQ ID NO: 21].

Xaa$^{21}$ is selected from the group consisting of Phe and Tyr. In some embodiments of the invention, Xaa$^{21}$ is Phe. [SEQ ID NO: 22] In other embodiments, Xaa$^{21}$ is Tyr [SEQ ID NO: 23]

Xaa$^{22}$ is selected from the group consisting of Ala, Ile, Leu and Val. Preferably, Xaa$^{22}$ is selected from the group consisting of Leu and Ile [SEQ ID NO: 24]. In some embodiments of the invention, Xaa$^{22}$ is Leu [SEQ ID NO: 25]. In other embodiments, Xaa$^{22}$ is Ile [SEQ ID NO: 26].

Xaa$^{23}$ is selected from the group consisting of Ala, Leu, Gly, Val and Ser. Preferably Xaa$^{23}$ is Ala [SEQ ID NO: 27].

Xaa$^{25}$ is selected from the group consisting of Arg and His. In some embodiments of the invention, Xaa$^{25}$ is Arg [SEQ ID NO: 28]. In other embodiments, Xaa$^{25}$ is His [SEQ ID NO: 29].

Xaa$^{30}$ is selected from the group consisting of His and Leu. In some embodiments of the invention, Xaa$^{30}$ is His [SEQ ID NO: 30]. In other embodiments, Xaa$^{30}$ is Leu [SEQ ID NO: 31].

In one preferred group of PYY analogues of the invention, Xaa$^2$ is Pro, Xaa$^{21}$ is selected from the group consisting of Phe and Tyr, and Xaa$^{22}$ is selected from the group consisting of Leu and Ile and Xaa$^{23}$ is Ala [SEQ ID NO: 32].

In one preferred group of PYY analogues Xaa$^{18}$ is selected from the group consisting of Leu and Ile, Xaa$^{21}$ is Tyr, Xaa$^{22}$ is selected from the group consisting of Ile and Leu, and Xaa$^{23}$ is Ala [SEQ ID NO: 33]. The residues at other positions may be as described above.

In another preferred group of PYY analogues of the invention, Xaa$^2$ is Pro, Xaa$^{21}$ is Tyr Xaa$^{22}$ is selected from the group consisting of Leu and Ile and Xaa$^{23}$ is Ala [SEQ ID NO: 34].

In a further preferred group of PYY analogues of the invention, Xaa$^2$ is Pro, Xaa$^{21}$ is Tyr, Xaa$^{22}$ is selected from the group consisting of Leu and Ile, Xaa$^{23}$ is Ala and Xaa$^{25}$ is Arg [SEQ ID NO: 35].

In another preferred group of PYY analogues of the invention, Xaa$^2$ is Pro, Xaa$^{18}$ is Leu, Xaa$^{21}$ is Tyr, Xaa$^{22}$ is Leu or Ile, Xaa²³ is Ala, Xaa²⁵ is Arg or His, and Xaa³⁰ is selected from the group consisting of His and Leu [SEQ ID NO: 47].

In a still further preferred group of PYY analogues of the invention, Xaa² is Pro, Xaa¹⁸ is Leu, Xaa²¹ is Tyr, Xaa²² is Leu or Ile, Xaa²³ is Ala, Xaa²⁵ is Arg and Xaa³⁰ is selected from the group consisting of His and Leu [SEQ ID NO: 36].

In a further preferred group of PYY analogues of the invention, Xaa² is Pro, Xaa¹⁸ is Leu, Xaa²¹ is Tyr, Xaa²² is Ile or Leu, Xaa²³ is Ala, Xaa²⁵ is Arg and Xaa³⁰ is Leu [SEQ ID NO: 37].

In one preferred embodiment of the invention, Xaa² is Pro, Xaa¹⁸ is Leu, Xaa²¹ is Tyr, Xaa²² is Ile or Leu, Xaa²³ is Ala, Xaa²⁵ is Arg and Xaa³⁰ is His [SEQ ID NO: 38].

In another preferred group of PYY analogues of the invention, Xaa² is Pro, Xaa²¹ is selected from the group consisting of Phe and Tyr, Xaa²² is selected from the group consisting of Leu and Ile and Xaa²³ is Ala and Xaa³⁰ is Leu [SEQ ID NO: 39].

In yet another preferred group of PYY analogues of the invention, Xaa² is Pro, Xaa²¹ is selected from the group consisting of Phe and Tyr, Xaa²² is selected from the group consisting of Leu and Ile, Xaa²³ is Ala and Xaa³⁰ is His [SEQ ID NO: 40].

In yet another preferred group of PYY analogues of the invention, Xaa² is Pro, Xaa²¹ is selected from the group consisting of Phe and Tyr, Xaa²² is selected from the group consisting of Leu and Ile, Xaa²³ is Ala, Xaa²⁵ is Arg, and Xaa³⁰ is Leu [SEQ ID NO: 41].

In yet another preferred group of PYY analogues of the invention, Xaa² is Pro, Xaa²¹ is selected from the group consisting of Phe and Tyr, Xaa²² is selected from the group consisting of Leu and Ile, Xaa²³ is Ala, Xaa²⁵ is Arg, and Xaa³⁰ is His [SEQ ID NO: 42].

In a still further preferred group of PYY analogues of the invention, Xaa² is Pro, Xaa²¹ is selected from the group consisting of Phe and Tyr, Xaa²² is selected from the group consisting of Ala and Ile, Xaa²³ is Ala, Xaa²⁵ is Arg, and Xaa³⁰ is His [SEQ ID NO: 43].

In one preferred embodiment of the invention, Xaa² is Pro, Xaa¹⁸ is Leu, Xaa²¹ is Tyr, Xaa²² is Ile, Xaa²³ is Ala, Xaa²⁵ is Arg and Xaa³⁰ is Leu [SEQ ID NO: 44].

PYY analogues of the formula (I) include, but are not limited to, the PYY analogues specifically described in the Examples and figures herein.

Compounds according to the present invention preferably have a more sustained effect on food intake reduction or have a stronger effect on food intake reduction than human PYY. Preferably they have an effect on food intake reduction which is at least as strong as native human PYY but which is more sustained. Increased duration of appetite suppression can be particularly important to avoid the effect known as "escape". A short duration of appetite suppressant may reduce appetite or the time covered by one meal and in that meal the subject typically eats less food. If, however, the appetite suppressant is then metabolized or otherwise removed from circulation as a subject then by the time the next meal the subject can regain its "normal" appetite. In view of the subject having eaten a small meal at the previous mealtime, the subject may in fact have an increased appetite at the time of the second meal. If the subject satisfies that appetite it is possible for the food intake over the two meals in total to be no lower than the food intake would have been without the appetite suppressant. That is to say, the subject may have "escaped" from the effects of the appetite suppressant. "Escape" can be reduced by using additional doses of appetite suppressant or by using an appetite suppressant with a longer duration of action. If the subject has a reduced appetite for longer, then the degree to which it can make up the deficit from one meal in the next meal is reduced and as there is a practical limit to total capacity in a particular single meal.

Preferably the compounds of the invention are selective for the Y2 receptor. That is say, they bind with a higher affinity to Y2 compared with other receptors such as Y1, Y3, Y4, Y5 and Y6. Those receptors are recognized based on binding affinity, pharmacology and sequence. Most, if not all, of the receptors are G protein coupled receptors. The Y1 receptor is generally considered to be postsynaptic and alleviates many of the known actions of neuropeptide Y in the periphery. Originally, this receptor was described as having poor affinity for C-terminal fragments of neuropeptide Y, such as the 13-36 fragment, but interacts with the full length neuropeptide Y and peptide YY with equal affinity (see PCT publication WO 93/09227).

Pharmacologically, the Y2 receptor is distinguished from Y1 by exhibiting affinity for C-terminal fragments of neuropeptide Y. The Y2 receptor is most often differentiated by the affinity of neuropeptide Y(13-36), although the 3-36 fragment of neuropeptide Y and peptide YY provides improved affinity and selectivity (see Dumont et al., *Society for Neuroscience Abstracts* 19:726, 1993). Signal transmission through both the Y1 and the Y2 receptors are coupled to the inhibition of adenylate cyclase. Binding to the Y2 receptor was also found to reduce the intracellular levels of calcium in the synapse by selective inhibition of N-type calcium channels. In addition, the Y2 receptor, like the Y1 receptors, exhibits differential coupling to second messengers (see U.S. Pat. No. 6,355,478), Y2 receptors are found in a variety of brain regions, including the hippocampus, substantia nigra-lateralis, thalamus, hypothalamus, and brainstem. The human, murine, monkey and rat Y2 receptors have been cloned (e.g., see U.S. Pat. No. 6,420,352 and U.S. Pat. No. 6,355,478).

An analogue of PYY according to the invention has preferably no overall ionic charge in solution (i.e., in a solution approximating to physiological conditions, such as, for example, those found in the tissue fluid or plasma). It is hypothesised that an absence of net charge under in vivo conditions limits its in vivo solubility and that this contributes to a slower absorption after subcutaneous administration of a high concentration peptide and thus prolonged presence in the circulation.

According to one preferred aspect of the invention, analogues of PYY 3-36 $NH_2$ according to the invention contain at least one of the amino acids corresponding to positions 4, 6, 19, 21, 25 or 30 in the native PYY 3-36 $NH_2$ molecule substituted for histidine. More preferably, more than one substitution to histidine is made. According to certain embodiments 2, 3 or 4 of the amino acid residues at positions 4, 6, 19, 21, 25 and 30 of the native PYY 3-36 $NH_2$ sequence are substituted for histidine residues. Preferably the total number of resultant histidine residues in the sequence of the claimed analogue is at least 2.

By way of further explanation, histidine is a unique amino acid in being not charged at pH 7.4 (i.e. under physiological conditions in the circulation or subcutaneously following subcutaneous administration). However, it is fully charged at pH 5 (or lower) since the pI of the NH side chain of histidine is about 6.0. According to certain preferred embodiments an analogue of PYY according to the invention has low or no overall charge at physiological pH (pH 7.4) and is preferably formulated as part of a composition having a pH of about pH5 (for example from pH4.5 to pH6.0—a lower pH than approximately pH 4 or 5 may be undesirable for an injectable composition because it is likely to increase pain at the injection site) so as to exhibit histidine ionisation and preferably an overall net change at such a lower pH. An increase in the number of charged residues increases the solubility of an injectable composition in the vial and therefore allows a small volume injection of a relatively concentrated peptide solution to be given. However, subsequent to subcutaneous injection the analogue is exposed to physiological pH at which the number of ionised residues and especially the number of ionised histidine residues falls and therefore solubility decreases. This causes the peptide to precipitate subcutaneously. The presence of His residues enhances this effect.

According to certain preferred embodiments, PYY analogues according to the invention have a combination of the following preferred features:

1) A peptide sequence which at pH 7.4 has no net charge and may have relatively few charged groups and hydrophilic groups overall to decrease intrinsic solubility.

2) The presence of a number of histidines which produce a net positive charge and good solubility at pH 5 for storage before administration and to allow a low viscosity administration solution (at pH 5).

3) Suitability for subcutaneous administration of a low volume and high concentration, exceeding the solubility constant at pH 7.4 but not at pH 5.

In addition to histidine being a particularly advantageous amino acid residue for this causing this differential pH-dependent solubility effect, the differential solubility of peptides containing histidine residues is greatly enhanced if formulated together with zinc ions. This is because zinc ions will bind to uncharged histidine residues in aqueous solution. It is believed that zinc ions are able to bind simultaneously to up to 4 uncharged histidines. This allows zinc to co-ordinate with histidine residues in several individual peptide molecules and thereby weakly cross-link the peptide molecule to other similar peptide molecules leading to a fall in solubility. However, zinc ions do not bind to charged histidine. Therefore, histidine containing peptides in a composition containing zinc ions will be cross-linked by weak ionic bonds at pH 7.4 but not at pH 5.0. The presence of His residues bound to zinc ions therefore enhances precipitation of the peptide after subcutaneous injection but does not affect solubility in the vial or syringe before administration. This means that a peptide having an overall pI of approximately 7 will have no charged residues at approximately neutral pH and a peptide comprising histidine residues in a formulation including zinc ions is advantageously soluble in the vial or syringe but precipitates subcutaneously following administration. So a pH7 neutral peptide with histidines in a formulation including zinc ions is advantageously soluble in the vial and syringe but precipitates subcutaneously following administration. Furthermore, zinc-enhanced precipitation is gradually reversible because the concentration of zinc ions following injection will fall as zinc ions are gradually washed out of the injection site. Therefore there is observed a delay in subcutaneous absorption with much better pharmacokinetics but no loss of bio-availability. The rate of absorption for a given histidine-containing neutral peptide can be controlled by the amount of zinc added.

Introduction of at least one additional histidine residue preferably results in the PYY analogues of the invention having at least one occurrence of two histidine residues separated from each other by 1 to 3 intervening amino acid residues (a pair of histidine residues). Such a spacing appears to be optimum for a single zinc ion to form in aqueous solution associations with both histidine residues in a pair. In one advantageous embodiment of the invention the amino acids at both positions 4 and 6 of the native PYY 3-36 NH$_2$ sequence are substituted for a histidine residue. In this embodiment, both of the histidine residues of a pair are artificially introduced with 1 intervening amino acid residue there between.

Preferably an analogue according to the invention has an overall pI of between 6.5 and 8.5. More preferably between 7.0 and 8.0, more preferably between 7.1 and 7.7, more preferably between 7.2 and 7.6, more preferably the analogue has an overall pI of approximately 7.4. This means that at physiological pH the analogue has no significant overall charge. The overall pI of a molecule may be calculated using techniques well known to a person skilled in the art or alternatively may be determined experimentally by using isoelectric focussing.

In order to take full advantage of this effect the Inventors have found that the following combination of features are particularly preferred.

1) Peptide sequence which at pH 7.4 has no net charge and relatively few charged groups and relatively few hydrophilic groups overall so as to decrease intrinsic solubility.

2) Presence of a number of histidines which produce a net positive charge and good solubility at pH 5 for storage before administration and to allow a low viscosity administration solution at pH 5.

3) Solubility for subcutaneous administration of a low volume high concentration exceeding the solubility constant at pH 7.4 but not at pH 5.

4) The presence of zinc ions which produce cross-linking of uncharged histidine residues at pH 7.4 and adjacent molecules but which do not cross-link charge histidine at pre-administration pH or approximately pH 5.

Variants:

Variants include PYY analogues of the invention comprising an amino acid sequence represented by formula (I) having up to two amino acids (e.g. 0, 1 or 2) other than Xaa$^2$, Xaa$^{18}$, Xaa$^{21}$, Xaa$^{22}$, Xaa$^{23}$, Xaa$^{25}$ and Xaa$^{30}$ replaced with a different amino acid (e.g., conservative substitutions and non-conservative substitutions; see, e.g., Table 2 below) which retain at least some of the activity of a corresponding non-variant molecule when in a molecule of the invention.

Typically conservative substitutions are the replacements, for one another, among the aliphatic amino acids Ala, Val, Leu and Ile; interchange of Ser and Thr containing hydroxy residues, interchange of the acidic residues Asp and Glu, interchange between the amide residues Asn and Gln, interchange of the basic residues Lys and Arg, interchange of the aromatic residues Phe and Tyr, and interchange of the small-sized amino acids Ala, Ser, Thr, Met and Gly. Guidance concerning how to make phenotypically silent amino acid substitutions, ie substitutions that do not alter the expressed phenotype, is provided in Bowie et al., *Science* 247:1306-1310, 1990.

TABLE 2

Non-limiting examples of conservative amino acid substitutions

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln |
| Met | Leu; Ile |

TABLE 2-continued

Non-limiting examples of conservative amino acid substitutions

| Original Residue | Conservative Substitutions |
|---|---|
| Phe | Met; Leu; Tyr |
| Ser | Thr |
| Thr | Ser |
| Trp | Tyr |
| Tyr | Trp; Phe |
| Val | Ile; Leu |

Variants further include PYY analogues in which up to two amino acids (e.g. 0, 1 or 2) other than $Xaa^2$, $Xaa^{18}$, $Xaa^{21}$, $Xaa^{22}$, $Xaa^{23}$, $Xaa^{25}$ and $Xaa^{30}$ are replaced with an amino acid present at the equivalent position in PYY derived from a species other than human. The sequences of PYYs of various species are included in Table 1 above.

Derivatives

A compound of the invention may comprise the structure of formula (I) modified by well known processes including amidation, glycosylation, carbamylation, acylation, for example acetylation, sulfation, phosphylation, cyclization, lipidization and pegylation. The structure of formula (I) may be modified at random positions within the molecule, or at predetermined positions within the molecule and may include one, two, three or more attached chemical moieties.

A compound of the invention may be a fusion protein, whereby the structure of formula (I) is fused to another protein or polypeptide (the fusion partner) using recombinant methods known in the art. Alternatively, such a fusion protein may be synthetically synthesized by any known method. Such a fusion protein comprises the structure of formula (I). Any suitable peptide or protein can be used as the fusion partner (e.g., serum albumin, carbonic anhydrase, glutathione-S-transferase or thioredoxin, etc.). Preferred fusion partners will not have an adverse biological activity in vivo. Such fusion proteins may be made by linking the carboxy-terminus of the fusion partner to the amino-terminus of the structure of formula (I) or vice versa. Optionally, a cleavable linker may be used to link the structure of formula (I) to the fusion partner. A resulting cleavable fusion protein may be cleaved in vivo such that an active form of a compound of the invention is released. Examples of such cleavable linkers include, but are not limited to, the linkers D-D-D-D-Y [SEQ ID NO: 45], G-P-R, A-G-G and H-P-F-H-L [SEQ ID NO: 46], which can be cleaved by enterokinase, thrombin, ubiquitin cleaving enzyme and renin, respectively. See, e.g., U.S. Pat. No. 6,410,707.

A compound of the invention may be a physiologically functional derivative of the structure of formula (I). The term "physiologically functional derivative" is used herein to denote a chemical derivative of a compound of formula (I) having the same physiological function as the corresponding unmodified compound of formula (I). For example, a physiologically functionally derivative may be convertible in the body to a compound of formula (I). According to the present invention, examples of physiologically functional derivatives include esters, amides, and carbamates; preferably esters and amides.

Pharmaceutically acceptable esters and amides of the compounds of the invention may comprise a $C_{1-20}$ alkyl-, $C_{2-20}$ alkenyl-, $C_{5-10}$ aryl-, $C_{5-10}$ ar-$C_{1-20}$ alkyl-, or amino acid-ester or -amide attached at an appropriate site, for example at an acid group. Examples of suitable moieties are hydrophobic substituents with 4 to 26 carbon atoms, preferably 5 to 19 carbon atoms. Suitable lipid groups include, but are not limited to, the following: lauroyl ($C_{12}H_{23}$), palmityl ($C_{15}H_{31}$), oleyl ($C_{15}H_{29}$), stearyl ($C_{17}H_{35}$), cholate; and deoxycholate.

Methods for lipidization of sulfhydryl-containing compounds with fatty acid derivatives are disclosed in U.S. Pat. No. 5,936,092; U.S. Pat. No. 6,093,692; and U.S. Pat. No. 6,225,445. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include, but are not limited to, the following: palmityl ($C_{15}H_{31}$), oleyl ($C_{15}H_{29}$), stearyl ($C_{17}H_{35}$), cholate; and deoxycholate.

Cyclization methods include cyclization through the formation of a disulfide bridge and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

A compound of the invention may be a pegylated structure of formula (I). Pegylated compounds of the invention may provide additional advantages such as increased solubility, stability and circulating time of the polypeptide, or decreased immunogenicity (see U.S. Pat. No. 4,179,337).

Chemical moieties for derivitization of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight, and may be branched or unbranched. For ease in handling and manufacturing, the preferred molecular weight of a polyethylene glycol for derivatisation of a compound of the invention is from about 1 kDa to about 100 kDa, the term "about" indicating that in preparations of polyethylene glycol, some molecules will weigh more, some less, than the stated molecular weight. Polymers of other molecular weights may be used, depending on the desired therapeutic profile, for example the duration of sustained release desired, the effects, if any on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

Salts of compounds of the invention that are suitable for use in a medicament are those wherein a counterion is pharmaceutically acceptable. However, salts having non-pharmaceutically acceptable counterions are within the scope of the present invention, for example, for use as intermediates in the preparation of the compounds of formula (I) and their pharmaceutically acceptable salts.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, $2^{nd}$ ed. R. Liu, CRC Press, page 553, which are incorporated herein by reference. Accordingly, it will be understood by the skilled person that the compounds of formula (I), as well as variants, derivatives and/or salts thereof may therefore be present in the form of solvates. Solvates of compounds of formula (I) which are suitable for use in medicine are those wherein the associated solvent is pharmaceutically acceptable. For example, a hydrate is an example of a pharmaceutically acceptable solvate. However, solvates having non-pharmaceutically acceptable associated solvents may find use as intermediates in the preparation of the compounds of formula (I) and their pharmaceutically acceptable salts thereof.

Conditions:

The invention provides a pharmaceutical composition comprising a compound of formula (I) together with a pharmaceutically acceptable carrier and optionally other therapeutic ingredients, together with related methods. In some embodiments, the pharmaceutical composition is present in a syringe or other administration device for subcutaneous administration to humans.

The invention further provides the compound of formula (I) or a variant, derivative, salt or solvate thereof for use as a medicament.

The invention also provides a compound of formula (I) or a variant, derivative, salt or solvate thereof, or a pharmaceutical composition comprising a compound of formula (I), for use in the treatment of obesity or diabetes. The invention further provides a compound of formula (I), or a pharmaceutical composition comprising a compound of formula (I), for use in reduction of appetite in a subject, for use in reduction of food intake in a subject, or for use in reduction of calorie intake in a subject.

The invention further provides the use of a compound of formula (I) or a variant, derivative, salt or solvate thereof for the manufacture of a medicament for the treatment of obesity or diabetes. The invention also provides the use of a compound of formula (I) or a variant, derivative salt or solvate thereof for the manufacture of a medicament for reducing appetite in a subject, reducing food intake in a subject, or reducing calorie intake in a subject.

The invention further provides a method of treating obesity or diabetes in a subject in need thereof comprising administering to the subject an effective amount of a compound of formula (I) or a variant, derivative, salt or solvate thereof, or a pharmaceutical composition comprising a compound of formula (I). The invention also provides a method of reducing appetite in a subject, reducing food intake in a subject, or reducing calorie intake in a subject, comprising administering to the subject an effective amount of a compound of formula (I), or a pharmaceutical composition comprising a compound of formula (I).

In some embodiments, the compound is administered parentally. In some embodiments, the compound is administered subcutaneously, intravenously, intramuscularly, intranasally, transdermally or sublingually.

The subject to whom the compound is administered may be overweight, for example, obese. Alternatively, or in addition, the subject may be diabetic, for example having insulin resistance or glucose intolerance, or both. The subject may have diabetes mellitus, for example, the subject may have Type II diabetes. The subject may be overweight, for example, obese and have diabetes mellitus, for example, Type II diabetes. Alternatively, the subject may have Type I diabetes. The compounds of the invention are thought to protect islet of Langerhans cells, in particular beta cells, allowing them to retain their normal physiological function, for example the ability to secrete insulin in response to appropriate simuli, when challenged by toxins (e.g. streptozotocin), pathogens or by an autoimmune response. The compounds of the invention are also thought to be effective in recovering or rescuing pancreatic islet function, and in particular beta cell function, deterioration of physiological function following exposure to a toxin, pathogen or an autoimmune response. Recovery of function may be to at least 10, 20, 30, 40, 50, 60, 70, 80, 90 or 100% of the function exhibited prior to deterioration. Accordingly, the invention also provides a compound of formula (I) or a variant, derivative, salt or solvate thereof, or a pharmaceutical composition comprising a compound of formula (I), for use in preventing loss of pancreatic islet function (for example beta cell function) and/or recovering pancreatic islet function (for example beta cell function). The invention further provides the use of a compound of formula (I) or a variant, derivative, salt or solvate thereof for the manufacture of a medicament preventing loss of pancreatic islet function (for example beta cell function) and/or recovering pancreatic islet function (for example beta cell function). The invention further provides a method of preventing loss of pancreatic islet function (for example beta cell function) and/or recovering pancreatic islet function (for example beta cell function) in a subject comprising administering to the subject an effective amount of a compound of formula (I) or a variant, derivative, salt or solvate thereof, or a pharmaceutical composition comprising a compound of formula (I). The invention also provide a pharmaceutical composition comprising a compound of formula (I) in combination with a second active ingredient which is a medicine (for example steptozotocin) which has as a side-effect islet toxicity.

In addition, or alternatively, the subject may have, or may be at risk of having, a disorder in which obesity or being overweight is a risk factor. Such disorders include, but are not limited to, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acnthosis nigricans; eczema; exercise intolerance; insulin resistance; hypertension hypercholesterolemia; cholithiasis; osteoarthritis; orthopedic injury; insulin resistance, for example, type 2 diabetes and syndrome X; and thromboembolic disease (see Kopelman, *Nature* 404:635-43; Rissanen et al., *British Med. J.* 301, 835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Furthermore, obesity is a recognized risk factor for increased incidence of complications of general anesthesia. (See e.g., Kopelman, *Nature* 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatititis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc.; large anterior abdominal wall masses, for example abdominal panniculitis with frequent panniculitis, impeding walking, causing frequent infections, odors, clothing difficulties, low back pain; musculoskeletal disease; pseudo tumor cerebri (or benign intracranial hypertension), and sliding hiatil hernia.

The present invention further provides a method for increasing energy expenditure in a subject. The method includes, for example, peripherally administering a therapeutically effective amount of a compound of the invention to the subject, thereby altering energy expenditure. Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect, the method of the invention involves manipulation of the arcuate circuitry, that alter food intake coordinately and reciprocally alter energy expenditure. Energy expenditure is a result of cellular metabolism, protein synthesis, metabolic rate, and calorie utilization. Thus, in this aspect of the invention, administration of a compound of formula (I) or a variant, derivative salt or solvate thereof results in increased energy expenditure, and decreased efficiency of calorie utilization.

The invention also provides a method for improving a lipid profile in a subject. The invention also provides a method for alleviating a condition or disorder that can be alleviated by reducing nutrient availability.

Appetite can be measured by any means known to one of skill in the art. For example, decreased appetite can be assessed by a psychological assessment. For example, administration of a compound of the invention results in a change in perceived hunger, satiety, and/or fullness. Hunger can be assessed by any means known to one of skill in the art. For example, hunger is assessed using psychological assays, such as by an assessment of hunger feelings and sensory perception using a questionnaire, such as, but not limited to, a Visual Analog Score (VAS) questionnaire. In one specific, non-limiting example, hunger is assessed by answering questions relating to desire for food, drink, prospective food consumption, nausea, and perceptions relating to smell or taste.

A compound of the invention may be used for weight control and treatment, for example reduction or prevention of obesity, in particular any one or more of the following: preventing and reducing weight gain; inducing and promoting weight loss; and reducing obesity as measured by the Body Mass Index. A compound of the invention may be used in the control of any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. A compound of the invention may be used in maintaining any one or more of a desired body weight, a desired Body Mass Index, a desired appearance and good health.

A subject may be a subject who desires weight loss, for example female and male subjects who desire a change in their appearance. A subject may desire decreased feelings of hunger, for example the subject may be a person involved in a lengthy task that requires a high level of concentration, for example soldiers on active duty, air traffic controllers, or truck drivers on long distance routes, etc.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

The invention relates to the treatment of metabolic disorders, for example disorders of energy metabolism. Such disorders include conditions or disorders associated with increased caloric intake include, but are not limited to, insulin resistance, glucose intolerance, obesity, diabetes, including type 2 diabetes, eating disorders, insulin-resistance syndromes, and Alzheimer's disease.

According to the present invention, a compound of formula (I) or a variant, derivative, salt or solvate thereof is preferably used in the treatment of a human. However, while the compounds of the invention will typically be used to treat human subjects they may also be used to treat similar or identical conditions in other vertebrates for example other primates;

farm animals for example swine, cattle and poultry; sport animals for example horses; companion animals for example dogs and cats.

Compositions

While it is possible for the active ingredient to be administered alone, it is preferable for it to be present in a pharmaceutical formulation or composition. Accordingly, the invention provides a pharmaceutical formulation comprising a compound of formula (I), or a variant or derivative thereof, or a salt or solvate thereof, as defined above and a pharmaceutically acceptable excipient. Pharmaceutical compositions of the invention may take the form of a pharmaceutical formulation as described below.

The pharmaceutical formulations according to the invention include those suitable for oral, parenteral (including subcutaneous, intradermal, intramuscular, intravenous, and intraarticular), inhalation (including fine particle dusts or mists which may be generated by means of various types of metered does pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2 S, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Preferably, compositions according to the invention are suitable for subcutaneous administration, for example by injection. According to certain embodiments the composition may contain metal ion for example copper, iron, aluminium, zinc, nickel or cobalt ions. The presence of such ions may limit solubility and thus delay absorption into the circulatory system from the site of subcutaneous administration. In a particularly preferred embodiment, the composition contains zinc ions. Zinc ions may be present at any suitable concentration for example at a molar ratio to peptide molecules of 10:1 to 1:10, 8:1 to 1:8, 5:1 to 1:5, 4:1 to 1:4, 3:1 to 1:3, 2:1 to 1:2 or 1:1.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate Telease tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) or variant, derivative, salt or solvate thereof can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to PYY and related molecules. Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention are also suitably administered as sustained-release systems. Suitable examples of sustained-release systems of the invention include suitable polymeric materials, for example semi-permeable polymer matrices in the form of shaped articles, e.g., films, or mirocapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracisternally; intravaginally; intraperitoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compound of formula (I). These compositions exhibit certain biocompatibility features which allow a controlled release of the active substance. See U.S. Pat. No. 5,700,486.

A compound of the invention may be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by a continuous subcutaneous infusions, for example, using a minipump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249:1527-1533, 1990). In another aspect of the disclosure, compounds of the invention are delivered by way of an implanted pump, described, for example, in U.S. Pat. No. 6,436,091; U.S. Pat. No. 5,939,380; U.S. Pat. No. 5,993,414.

Implantable drug infusion devices are used to provide patients with a constant and long term dosage or infusion of a drug or any other therapeutic agent. Essentially such device may be categorized as either active or passive. A compound of the present invention may be formulated as a depot preparation. Such a long acting depot formulation can be administered by implantation, for example subcutaneously or intramuscularly; or by intramuscular injection. Thus, for example, the compounds can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of a compound of the invention may be administered as a single pulse dose, as a bolus dose, or as pulse doses administered over time. Thus, in pulse doses, a bolus administration of a compound of the invention is provided, followed by a time period wherein no a compound of the invention is administered to the subject, followed by a second bolus administration. In specific, non-limiting examples, pulse doses of a compound of the invention are administered during the course of a day, during the course of a week, or during the course of a month.

In one embodiment, a therapeutically effective amount of a compound of the invention is administered with a therapeutically effective amount of another agent, for example an additional appetite suppressant, a food-intake-reducing, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, and fluoxetine. The compound of the invention can be administered simultaneously with the additional appetite suppressant, or it may be administered sequentially. Thus, in one embodiment, the compound of the invention is formulated and administered with an appetite suppressant as a single dose.

A compound of the invention may be administered whenever the effect, e.g., appetite suppression, decreased food intake, or decreased caloric intake, is desired, or slightly before to whenever the effect is desired, such as, but not limited to about 10 minutes, about 15 minutes, about 30 minutes, about 60 minutes, about 90 minutes, or about 120 minutes, before the time the effect is desired.

The therapeutically effective amount of a compound of the invention will be dependent on the molecule utilized, the subject being treated, the severity and type of the affliction, and the manner and route of administration. For example, a therapeutically effective amount of a compound of the invention may vary from about 0.01 µg per kilogram (kg) body weight to about 1 g per kg body weight, for example about 0.1 µg to about 20 mg per kg body weight, for example about 1 µg to about 5 mg per kg body weight, or about 5 µg to about 1 mg per kg body weight.

In one embodiment of the invention, a compound of the invention may be administered to a subject at from 5 to 1000 nmol per kg bodyweight, for example at from 10 to 750 nmol per kg bodyweight, for example at from 20 to 500 nmol per kg bodyweight, in particular at from 30 to 240 nmol per kg bodyweight. For a 75 kg subject, such doses correspond to dosages of from 375 nmol to 75 µmol, for example from 750 nmol to 56.25 mmol, for example from 1.5 to 37.5 mmol, in particular from 2.25 to 18 mmol.

In an alternative embodiment, a compound of the invention may be administered to a subject at 0.5 to 135 picomole (pmol) per kg body weight, for example 5 to 100 picomole (pmol) per kg body weight, for example 10 to 90 picomole (pmol) per kg body weight, for example about 72 pmol per kg body weight. In one specific, non-limiting example, a compound of the invention is administered in a dose of about 1 nmol or more, 2 nmol or more, or 5 nmol or more. In this example, the dose of the compound of the invention is generally not more than 100 nmol, for example, the dose is 90 nmols or less, 80 nmols or less, 70 nmols or less, 60 mmols or less, 50 nmols or less, 40 nmols or less, 30 nmols or less, 20 nmols or less, 10 nmols. For example, a dosage range may comprise any combination of any of the specified lower dose limits with any of the specified upper dose limits. Thus, examples of non-limiting dose ranges of compounds of the invention are within the range of from 1 to 100 nmols, from 2 to 90 mols, from 5 to 80 nmols.

In one specific, non-limiting example, from about 1 to about 50 nmol of a compound of the invention is administered, for example about 2 to about 20 nmol, for example about 10 nmol is administered as a subcutaneous injection. The exact dose is readily determined by one of skill in the art based on the potency of the specific compound utilized, the route of delivery of the compound and the age, weight, sex and physiological condition of the subject.

Suitable doses of compounds of the invention also include those that result in a reduction in calorie intake, food intake, or appetite, or increase in energy expenditure that is equivalent to the reduction in calorie intake, food intake, or appetite, or to increase the energy expenditure, caused by the normal postprandial level of PYY. Examples of doses include, but are not limited to doses that produce the effect demonstrated when the serum levels of PYY are from about 40 pM to about 60 pM, or from about 40 pM to about 45 pM, or about 43 pM.

The doses discussed above may be given, for example, once, twice, three-times or four-times a day. Alternatively, they may be give once every 2, 3 or 4 days. In a slow release formulation containing zinc, it may be possible to give a dose once every 3, 6, 7, 8, 9, 10, 11, 12, 13, 14, 15, 16, 17, 18, 19, 20 or 21 days. According to certain embodiments they may be administered once shortly before each meal to be taken.

Specific Sequences of the Invention

According to certain specific embodiments of the invention the analogue of PYY has an amino acid sequence given in one of the specific sequences set out in FIG. 1.

The invention is illustrated by the following non-limiting Examples.

8. EXAMPLES

Materials and Methods

Animals

Male C57BL/6 mice (Harlan) were used for all mouse experiments. Male Wistar rats (Charles River) were used for all rat experiments.

Peptide Synthesis

Peptides were made by a standard automated fluorenyl-methoxycarbonyl (Fmoc) solid phase peptide synthesis (SPPS) method. Peptide synthesis was carried out on a tryclic amide linker resin. Amino acids were attached using the Fmoc strategy. Each amino acid was added sequentially from the C— to the N-termini. Peptide couplings were mediated by the reagent TBTU. Peptide cleavage from the resin was achieved with trifluoracetic acid in the presence of scavengers. Native PYY 3-36 $NH_2$ is obtained as described previously (WO03/026591); de novo synthesis using tryclic amide resin and Fmoc chemistry is also possible.

Peptides were purified by reverse phase HPLC. Full quality control was performed on all purified peptides and peptides were shown to be greater than 95% pure by HPLC in two buffer systems. Amino acid analysis following acid hydrolysis confirmed the amino acid composition. MALDI-MS showed the expected molecular ion.

Example 1

Binding Studies

Membrane preparation of HEK 293 cells overexpressing the human Y2 receptor (NPYR200000, Missouri S&T cDNA resource centre) were isolated by osmotic lysis and differential centrifugation as described by Morgan et al (Morgan D G, Lambert P D, Smith D M, Wilding J P H & Bloom S R. J. Reduced NPY induced feeding in diabetic but not steroid treated rats: lack of evidence for changes in receptor number or affinity. Neuroendocrinol 1996. 8 283-290). Receptor binding assays were completed as described by Druce et al (Druce M R, Minnion J S, Field B C, Patel S R, Shillito J C, Tilby M, Beale K E, Murphy K G, Ghatei M A & Bloom S R. Investigation of structure-activity relationships of oxyntomodulin (oxm) using oxm analogues. 2009 Endocrinology 150(4) 712-22) except the buffer used was 0.02M HEPES pH 7.4, 5 mM $CaCl_2$, 1 mM $MgCl_2$, 1% bovine serum albumin, 0.1 mM diprotin A, 0.2 mM PMSF, 10 µM phosphoramidon, $^{125}$I-$PYY_{1-36}$ as the radiolabel and the human Y2 receptor used.

Acute Feeding Studies in Mice

Mice were individually housed in IVC cages. Animals were randomised into treatment groups, with stratification by body weight. Mice were fasted overnight (16 hrs) prior to peptide or vehicle administration. All peptide solutions were prepared freshly, immediately prior to administration. The vehicle used for all studies was 5% v/v water and 95% v/v sodium chloride (0.9% w/v). Peptide and vehicle were administered by subcutaneous injection, with dosage corrected for bodyweight. The maximal injection volume was 100 µl. Vehicle or peptide was administered at 09:00 and animals were returned to their home cage with a known amount of food. Food intake was measured at 1, 2, 4, 8 and 24 hours post injection. All statistics are calculated using a one-way ANOVA with Dunnett's post-test or one-way ANOVA with Bonferroni post-test.

Results

FIG. 1 shows the amino acid sequences of example PYY analogues of the invention (Analogue Nos. 1-3), the result of binding experiments, and the results of experiments in which the appetite suppressant effects in mice of compounds of the invention have been compared with human PYY 3-36 $NH_2$. The first column contains the Analogue number, and the second column contains a Reference number. Subsequent columns show the amino acid sequence of each example PYY analogue. The column headed "Binding Ratio" shows strength of binding to the human Y2 Receptor of each example PYY analogue relative to human PYY 3-36 $NH_2$. A value of greater than 1.0 indicates binding to the human Y2 receptor greater than that shown by human PYY 3-36 $NH_2$. The column headed "Food Intake Ratio" shows the reduction in food intake relative to saline during the time period 0 to 24 hours (time measured from administration of peptide) for each example PYY analogue, expressed as a ratio to the reduction in food intake relative to saline shown by animals administered native human PYY 3-36 $NH_2$. A value of greater than 1.0 indicates a reduction of food intake better than that achieved with human PYY 3-36 $NH_2$.

Example 2

In Vivo Pharmacokinetic Studies

Materials and Methods

Male Wistar rats were injected subcutaneously with analogues 1, 2 or 3 having the sequences given in FIG. 1.

Each injection was of 1 mg peptide per rat at a concentration of 50 mg/ml of peptide and of 1 zinc ion (as $ZnCl_2$) per peptide molecule.

Rats were decapitated and trunk blood collected at 4 h, 1 day, 2 days, 4 days and 7 or 8 days. Blood was also collected from 2 rats not injected with peptide in order to ascertain basal (endogenous) PYY levels.

Plasma peptide levels were measured by a general PYY RIA using the same analogue as a standard as that which was being measured in each case.

Results

Figure 3:
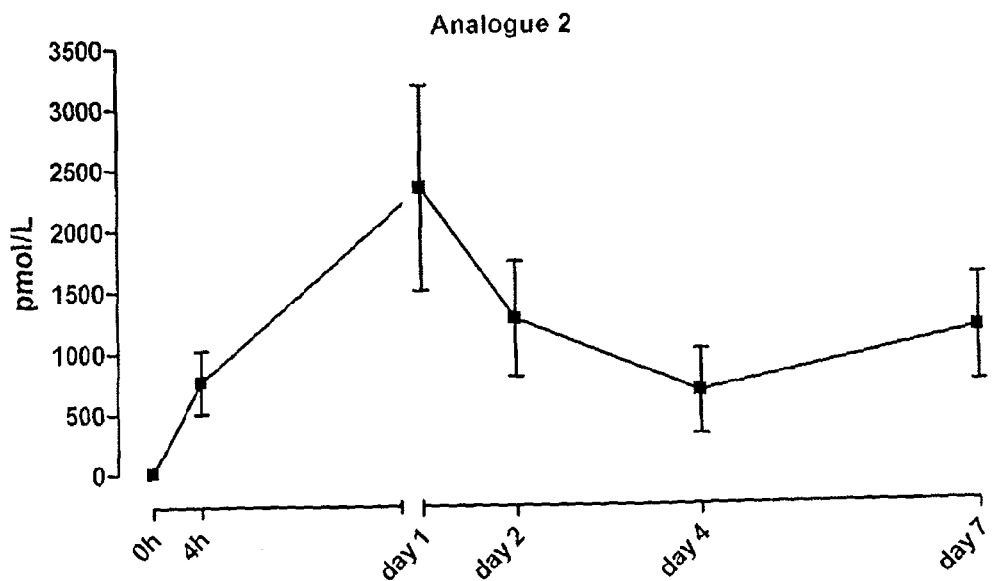
Figure 4:
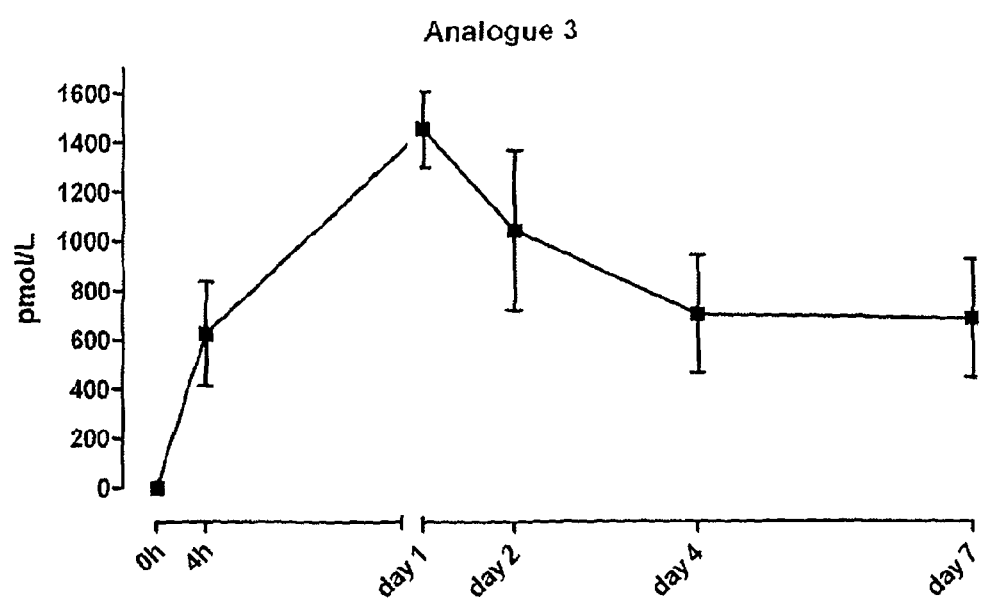

Results are presented in FIGS. 2, 3 and 4. Despite endogenous PYY having a half life of only several minutes, the level of circulating analogue remains elevated at for several days.

Example 3

DIO male C57BL/6 mice having a mean starting weight of 38 g were injected daily with either vehicle (n=12) or analogue 2 (30 nmol/kg (days 1 to 6), followed by 60 nmol/kg) (n=10). The peptide was administered with zinc ions in the form of zinc chloride, and the formulation contained 1 zinc ion per molecule of peptide. Food intake and body weight were measured daily.

Results

Figure 5:
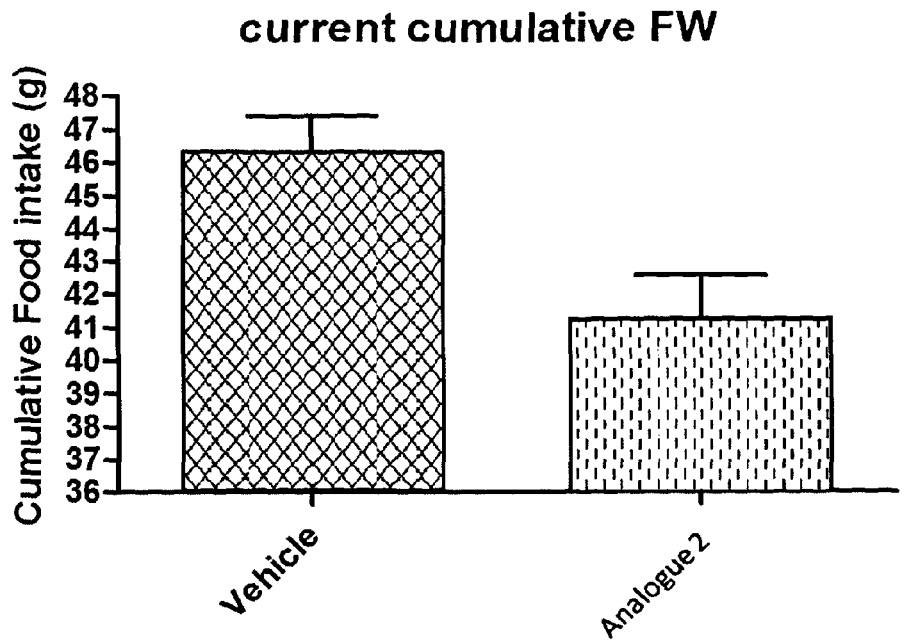
FIGS. 5 and 6 show the results of chronic administration of a compound of the invention to overweight mice described in Example 3.
Figure 6:
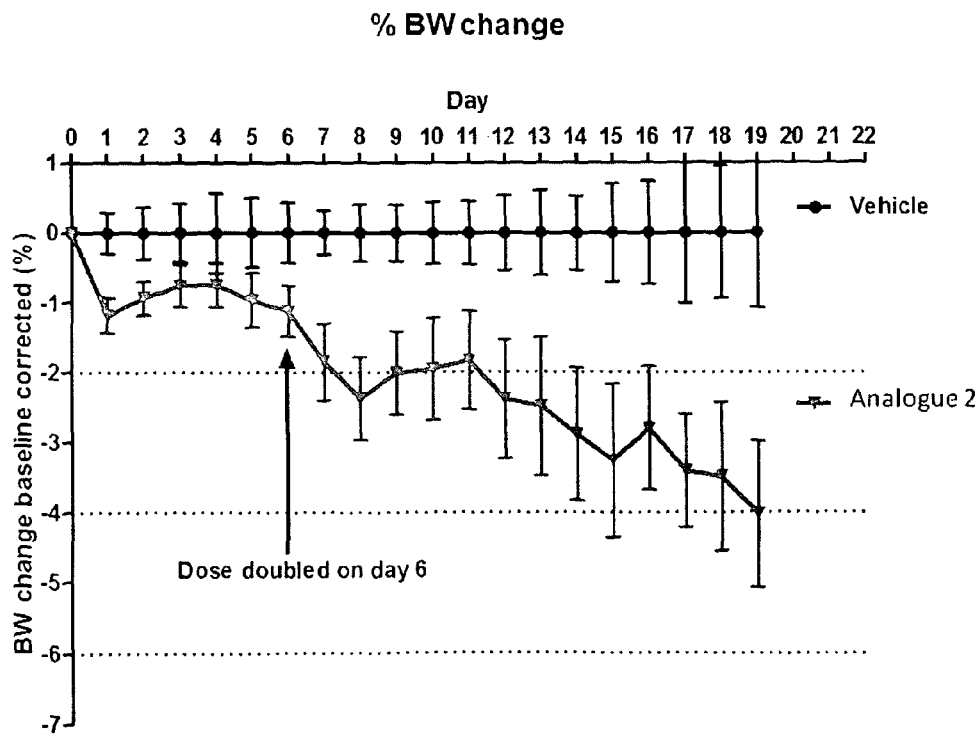

The results of the feeding studies are shown in FIGS. 5 and 6. FIG. 5 shows cumulative food intake (in grams) for mice receiving either vehicle or analogue 2. FIG. 5 shows that cumulative food intake was lower for mice receiving a compound of the invention than for mice receiving vehicle. FIG. 6 shows the percent change in body weight for mice receiving analogue 2 as compared with mice receiving vehicle. FIG. 6 shows that mice receiving a compound of the invention had lower body weight (~4% lower) than mice receiving vehicle.

The invention claimed is:

1. An analogue of peptide YY (PYY) comprising an amino acid sequence represented by formula (I)

(I)
[SEQ ID NO: 1]
Xaa²-Ile-His-Pro-His-Ala-Pro-Gly-Glu-Asp-Ala-Ser-

Pro-Glu-Glu-Leu-Xaa¹⁸-His-Tyr-Xaa²¹-Xaa²²-Xaa²³-

Leu-Xaa²⁵-His-Tyr-Leu-Asn-Xaa³⁰-Val-Thr-Arg-Gln-

Arg-Tyr-NH₂ wherein
Xaa² is selected from the group consisting of Pro and Gly;
Xaa¹⁸ is selected from the group consisting of Leu, Ile and Lys;
Xaa²¹ is selected from the group consisting of Tyr and Phe;
Xaa²² is selected from the group consisting of Ile, Leu, Ala and Val;
Xaa²³ is selected from the group consisting of Ala, Leu, Gly, Val and Ser;
Xaa²⁵ is selected from the group consisting of Arg and His; and
Xaa³⁰ is selected from the group consisting of Leu and His;
or a compound that is a variant and/or derivative thereof;
or a salt thereof, including a salt of such a variant and/or derivative,
a variant being an amino acid sequence having up to two amino acids other than Xaa², Xaa¹⁸, Xaa²¹, Xaa²², Xaa²³, Xaa²⁵ and Xaa³⁰ replaced with a different amino acid.

2. An analogue of PYY as claimed in claim 1 which is not a variant.

3. An analogue of PYY as claimed in claim 1, wherein Xaa² is Pro [SEQ ID NO: 18].

4. An analogue of PYY as claimed in claim 1, wherein Xaa¹⁸ is Leu [SEQ ID NO: 21].

5. An analogue of PYY as claimed in claim 1, wherein
Xaa² is Pro
Xaa¹⁸ is Leu;
Xaa²¹ is Tyr;
Xaa²² is Ile or Leu;
Xaa²³ is Ala;
Xaa²⁵ is selected from the group consisting of Arg or His; and
Xaa³⁰ is selected from the group consisting of Leu and His [SEQ ID NO: 47].

6. An analogue of PYY as claimed in claim 1, wherein Xaa²⁵ is Arg [SEQ ID NO: 28].

7. An analogue of PYY as claimed in claim 1, wherein Xaa²² is Ile [SEQ ID NO: 26].

8. An analogue of PYY as claimed in claim 1, wherein Xaa²² is Leu [SEQ ID NO: 25].

9. An analogue of PYY as claimed in claim 1, wherein Xaa³⁰ is Leu [SEQ ID NO: 31].

10. An analogue of PYY as claimed in claim 1 which is a derivative that has been modified by one or more processes selected from amidation, glycosylation, carbamylation, acylation, sulfation, phosphylation, cyclization, lipidization and pegylation.

11. An analogue of PYY as claimed in claim 1 which is a derivative that is a fusion protein.

12. An analogue of PYY as claimed in claim 11 that is produced by a recombinant method.

13. An analogue of PYY as claimed in claim 11 that is produced by a synthetic method.

14. An analogue of PYY as claimed in claim 1 for use as a medicament.

15. A pharmaceutical composition comprising an analogue of PYY as claimed in claim 1 together with a pharmaceutically acceptable carrier and optionally other therapeutic ingredients.

16. A pharmaceutical composition as claimed in claim 15, present in a syringe or other administration device for subcutaneous administration to humans.

17. An analogue of PYY as claimed in claim 1, wherein the amino acid sequence is selected from the group consisting of SEQ ID NOS: 44 and 48 to 57.

18. A pharmaceutical composition as claimed in claim 15, wherein the amino acid sequence is selected from the group consisting of SEQ ID NOS: 18, 21, 25-26, 28, 31, 44 and 47 to 57.

19. A pharmaceutical composition as claimed in claim 16, wherein the amino acid sequence is selected from the group consisting of SEQ ID NOS: 18, 21, 25-26, 28, 31, 44 and 47 to 57.

\* \* \* \* \*